(12) United States Patent
Bettsworth et al.

(10) Patent No.: US 11,029,312 B2
(45) Date of Patent: *Jun. 8, 2021

(54) STABILIZATION OF GLUTAMATE DEHYDROGENASE IN AN AQUEOUS SOLUTION

(71) Applicant: BIOMERIEUX, Marcy l'Etoile (FR)

(72) Inventors: Florence Bettsworth, Dommartin (FR); Jérôme Martinez, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/733,681

(22) Filed: Jan. 3, 2020

(65) Prior Publication Data
US 2020/0132690 A1 Apr. 30, 2020

Related U.S. Application Data

(63) Continuation of application No. 15/038,554, filed as application No. PCT/FR2014/053213 on Dec. 8, 2014, now Pat. No. 10,533,999.

(30) Foreign Application Priority Data

Dec. 10, 2013 (FR) ...................................... 1362354

(51) Int. Cl.
| | | |
|---|---|---|
| *G01N 33/573* | (2006.01) | |
| *C12N 9/06* | (2006.01) | |
| *C12N 9/96* | (2006.01) | |
| *C12Q 1/04* | (2006.01) | |
| *C12Q 1/32* | (2006.01) | |

(52) U.S. Cl.
CPC ......... *G01N 33/573* (2013.01); *C12N 9/0016* (2013.01); *C12N 9/96* (2013.01); *C12Q 1/04* (2013.01); *C12Q 1/32* (2013.01); *C12Y 104/01002* (2013.01); *G01N 2333/33* (2013.01); *G01N 2333/90616* (2013.01)

(58) Field of Classification Search
None
See application file for complete search history.

(56) References Cited

U.S. PATENT DOCUMENTS

| 5,965,375 | A | * | 10/1999 | Valkirs ...................... C12Q 1/32 435/26 |
| 10,533,999 | B2 | * | 1/2020 | Bettsworth .......... C12N 9/0016 |
| 2004/0086532 | A1 | | 5/2004 | Donovan |
| 2010/0028372 | A1 | * | 2/2010 | Jezek .................... A61K 39/292 424/184.1 |

FOREIGN PATENT DOCUMENTS

| FR | 2781802 A1 | 2/2000 |
| WO | 95/08000 A2 | 3/1995 |
| WO | 98/45706 A1 | 10/1998 |
| WO | 2007/003936 A1 | 1/2007 |
| WO | 2008/084237 A2 | 7/2008 |
| WO | 2009/006301 A2 | 1/2009 |

OTHER PUBLICATIONS

Anderson BM et al."Purification and Characterization of Clostridium difficile Glutamate Dehydrogenase," Archives of Biochemistry and Biophysics. Jan. 1993, pp. 483-488, vol. 300, No. 1.
Boersma YL, Plückthun A. "DARPins and other repeat protein scaffolds: advances in engineering and applications," Current Opinion in Biotechnology, Jun. 27, 2011, pp. 849-857.
Eckert C. et al. "Diagnostic des infections a Clostridium difficile," Journal des Anti-Infectieux, Mar. 4, 2011, pp. 67-73, vol. 13.
Ellington AD and Szostak JW. "In Vitro Selection of RNA Molecules that Bind Specific Ligands," Nature, Aug. 30, 1990, pp. 818-822, vol. 346, Nature Publishing Group.
Garcia-Galan C. et al. "Stabilization of the hexameric glutamate dehydrogenase from *Escherichia coli* by cations and polyethyleneimine," Enzyme and Microbial Technology, Feb. 21, 2013, pp. 211-217, vol. 52, No. 4-5.
Van Den Broek et al. "Bioanalytical LC-MS/MS of protein-based biopharmaceuticals," Journal of Chromatography B, Apr. 20, 2013, pp. 161-179, vol. 929.
Lilley K. et al. "The essential active-site lysines of clostridial glutamate dehydrogenase A study with pyridoxial-5'-phosphate," European Journal of Biochemistry, Apr. 21, 1992, pp. 533-540, vol. 207, No. 2.
Maurizi M. et al. "Degradation of L-Glutamate Dehydrogenase from *Escherichia coli*: Allosteric Regulation of Enzyme Stability," Archives of Biochemistry and Biophysics, Oct. 29, 2001, pp. 206-216, vol. 397, No. 2.
Mar. 18, 2015 Written Opinion issued in International Patent Application No. PCT/FR2014/053213.
Kaushik et al. 1998 (Thermal Stability of Proteins in Aqueous Polyol Solutions: Role of the Surface Tension of Water in the Stabilising Effect of Polyols; J. Phys. Chem. 102: 7058-7066) (Year: 1998).

(Continued)

*Primary Examiner* — Mary Maille Lyons
(74) *Attorney, Agent, or Firm* — Oliff PLC

(57) ABSTRACT

An aqueous composition includes (i) glutamate dehydrogenase from a bacterium of the *Clostridium* genus, (ii) a stabilizing compound that is a carboxylic acid having a carbon-based chain of at least three carbon atoms and comprising at least two —COOH groups, or a salt thereof, and (iii) any of a monosaccharide polyol, disaccharide polyol, or polymeric macromolecule in addition to the glutamate dehydrogenase. A process for stabilizing the glutamate dehydrogenase in order to maintain antigenic properties of the glutamate dehydrogenase includes stabilizing the glutamate dehydrogenase in the aqueous composition and maintaining the antigenic properties of the glutamate dehydrogenase during storage of the aqueous composition.

29 Claims, 2 Drawing Sheets

Figure 1:
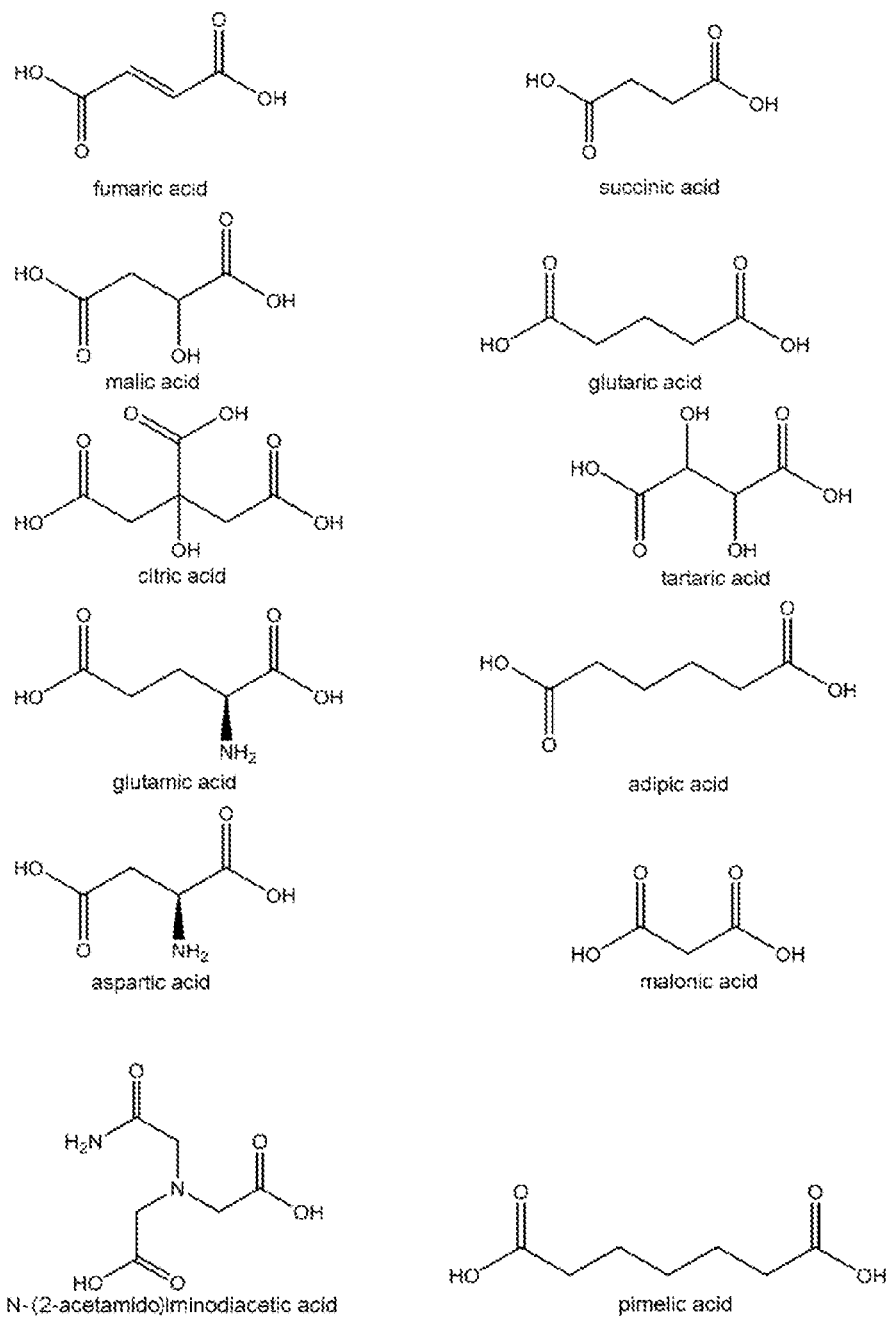

Specification includes a Sequence Listing.

(56) References Cited

OTHER PUBLICATIONS

Kaushik et al. 1999 (A mechanistic analysis of the increase in the thermal stability of proteins in aqueous carboxylic acid salt solutions; Protein Science 8:222-233) (Year: 1999).
Pierce Technical Resource 2005 (Protein stability and storage; www.piercenet.com; Rockford, IL pp. 1-3). (Year: 2005).
Aghajanian et al. 1995 (Urea-induced inactivation and denaturation of clostridial glutamate dehydrogenase: the absence of stable dimeric or trimeric intermediates; Biochem J. 311:905-910) (Year: 1995).
Lyerly et al. 1991 (Identification of the Latex Test-Reactive Protein of Clostridium difficile as Glutamate Dehydrogenase; J of Clinical Microbiology 29 (11): 2639-2642) (Year: 1991).

\* cited by examiner

STABILIZATION OF GLUTAMATE DEHYDROGENASE IN AN AQUEOUS SOLUTION

This is a Continuation of application Ser. No. 15/038,554 filed May 23, 2016, which is a National Stage Entry of PCT/FR2014/053213 filed Dec. 8, 2014, which claims priority to FR 1362354 filed Dec. 10, 2013. The disclosures of the prior applications are hereby incorporated by reference herein in their entireties.

The present invention relates to the field of the in vitro detection of bacterial proteins in biological samples that may contain these proteins. In particular, the invention relates to the stabilization of glutamate dehydrogenase from a bacterium of the *Clostridium* genus so that this protein retains the antigenic properties thereof when it is in an aqueous solution.

Bacteria of the *Clostridium* genus are Gram-positive, sporulated, anaerobic bacteria which are incapable of reducing sulfates to sulfites. Some species are very pathogenic, such as *Clostridium difficile, Clostridium botulinum* and *Clostridium perfringens*, these being the most well-known.

The *Clostridium difficile* bacterium is the main agent responsible for diarrhea following the administration of antibiotics. It is formidable because of its very high contagion potential. Although approximately 5% of the population are asymptomatic carriers of the bacterium, its pathological manifestations are closely linked to time spent in hospital. This bacterium develops in an intestinal flora weakened by treatment with antibiotics and can secrete two toxins, A and B. Only the toxin-producing strains are pathogenic. Toxin A, an enterotoxin, causes modification of intestinal epithelium permeability; toxin B, a cytotoxin, directly attacks the cells of the epithelium. The combined effect of the two toxins is a decrease in intestinal transit time and in intestinal absorption, thereby resulting in diarrhea. More rarely, the *Clostridium difficile* bacterium can cause a severe inflammation of the colon (pseudomembraneus colitis).

The *Clostridium botulinum* bacterium, for its part, is responsible for botulism. It produces spores which represent the resistance form of the bacterium. These spores can withstand weak heat treatments, such as pasteurization, which can pose food safety problems, and can then give a metabolically active bacterial cell capable of multiplying. This bacterium secretes one of the most powerful toxins of the living world, the botulinum toxin. Active by ingestion, this toxin then diffuses in the organism and acts by blocking neuromuscular transmission: it inhibits the motor neurons of muscle contraction. This infection can cause death by paralysis of the respiratory muscles if no treatment is put in place.

The *Clostridium perfringens* bacterium is a bacterium which develops in wombs, sometimes very deeply. This bacterium will produce necrotoxins, thus causing necrotizing enteritis. The most common major toxin is the alpha toxin, essentially produced by *Clostridium perfringens* type A. This toxin is involved in a very large number of cases of gangrene in humans and animals. Alone or in combination with other toxins, it also causes abrupt mortalities in pigs and ruminants.

The detection of the presence of these bacteria and of the secretion of their toxin is therefore a major public health problem which requires laboratories to have detection tests that are reliable, both in terms of sensitivity/specificity, and in terms of reproducibility of the results obtained with these tests. To do this, laboratories in particular need tests which include reagents that do not degrade over time and therefore remain stable.

The detection of the presence of bacteria in samples can be carried out by various techniques, such as the use of culture media or the technique of immunoassays, which are widely known to those skilled in the art. The immunoassay technique is a technique consisting broadly in detecting the presence of proteins using binding partners of these proteins. In the context of the detection of bacteria of the *Clostridium* genus, one of the detectable proteins, representative of the presence of this bacterium, is glutamate dehydrogenase (GDH). Other detectable proteins are the toxins secreted when the bacteria are toxigenic. The detection or quantification of GDH by immunoassay is a technique which makes it possible to have a greater diagnostic sensitivity than the detection or quantification of toxins by immunoassay. It is used as a screening means on populations at risk. In the event of a positive result, a search for toxins is then recommended since this technique has, for its part, a greater specificity.

Several diagnostic companies propose kits for detecting GDH in *Clostridium difficile*. Mention may, for example, be made of the VIDAS® GDH kit from the applicant.

In addition to the binding partners, the immunoassay technique also requires the use of reagents for calibrating and/or controlling the test. Thus, in the context of a GDH immunoassay, such reagents comprise GDH as such, which must retain its antigenic properties for as long as required from the viewpoint of the shelf life of the diagnostic kit in which it is contained.

The properties of a protein can be disrupted by any structural modification, both from a chemical point of view and from a physical point of view. The chemical modifications of a protein are based on changes at the level of the covalent bonds, due for example to oxidation, hydrolysis, etc., reactions, while the physical modifications, also called denaturation, cause a disorganization of the tertiary structure or three-dimensional conformation of the protein, without breaking of the covalent bonds. Protein denaturation can be induced by many chemical or physical factors, such as, inter alia, temperature, pH modification or a chemical agent. The consequence of such modifications is a disruption of the protein's actual activity. Thus, in the context of an enzyme such as GDH, such modifications can modify its enzymatic activity, something which the various authors have tried to overcome.

Thus, for example, the authors of patent application WO 2007/003936 have described the stabilization of the enzymatic activity of various proteins using one or more stabilizing compounds having the following characteristics:

They have ionizable groups capable of proton exchange with the protein to be stabilized and with the ionized products of the aqueous solution, The ionizable groups include first groups which are positively charged when they are protonated and uncharged when they are deprotonated, and second groups which are uncharged when they are protonated and negatively charged when they are deprotonated, and The pH of the composition is maintained in a range of +/−0.5 pH units of the pH at which the composition has its maximum stability relative to the pH.

This document indicates that the enzymatic activity of bovine GDH is preserved by adding lysine as stabilizing compound, whereas the addition of citrate does not allow GDH to retain this enzymatic activity.

Garcia-Galan C. et al., 2013, have for their part indicated that *Escherichia coli* GDH can be stabilized so that it maintains its enzymatic activity by coating the surface of the GDH with polyethyleneimine in the presence of lithium$^+$.

However, no author has shown an interest in searching for how to stabilize GDH so that it retains its antigenic properties, although this is a problem encountered when this protein is used in an aqueous solution, in particular in a very dilute manner, for example at a concentration of about a few ng/ml.

Indeed, GDH is usually stored in lyophilized form since it is known that it does not retain its antigenic properties when it is placed in an aqueous solution. Thus, when GDH must be placed in an aqueous solution, for example in the context of a GDH immunoassay, the laboratory assistant takes up the lyophilized GDH in an aqueous solvent, and prepares aliquots that must then be frozen at −20° C. The expiration date of the aqueous solution is then quite short, on average two months stored between 2 and 8° C. Furthermore, taking up the GDH in an aqueous buffer has the drawbacks of leading not only to additional manipulations, but also to additional risks of error when it is taken up. Finally, this also requires the presence of a freezer.

The applicant has found, against all expectations, that it is possible to stabilize GDH in an aqueous solution so that its three-dimensional structure is at least partly preserved such that it keeps its antigenic properties. Such a stabilization is carried out by addition, as stabilizing compound, of a carboxylic acid having a carbon-based chain of at least three carbon atoms and comprising at least two —COOH groups, or of a salt thereof. By virtue of the addition of this compound, the aqueous solution comprising the GDH can be stored between 2 and 8° C., for many months.

Thus, a first subject of the invention relates to a process for stabilizing glutamate dehydrogenase from a bacterium of the *Clostridium* genus in order to maintain the antigenic activity thereof, comprising the step of mixing, with said glutamate dehydrogenase in an aqueous solution, a stabilizing compound which is a carboxylic acid having a carbon-based chain of at least three carbon atoms and at least two —COOH groups, or a salt thereof.

Another subject of the invention relates to the stabilized aqueous compositions thus obtained, and also to the diagnostic kits comprising these compositions.

Yet another subject of the invention relates to the use of the compositions for establishing standard ranges in the context of a GDH immunological assay.

Yet another subject of the invention relates to the use of the compositions as a calibrator and/or control in the context of a GDH immunological assay.

Finally, a last subject of the invention relates to the processes for detecting the presence of a bacterium of the *Clostridium* genus using a composition of the invention, the bacterium being, where appropriate, toxigenic.

The applicant has therefore shown, against all expectations, that the use of specific compounds makes it possible to stabilize GDH from bacteria of the *Clostridium* genus in order to maintain the antigenic properties thereof when the GDH is in an aqueous solution, in particular in concentrations of about a few ng/ml, for example from 0.75 to 10 ng/ml, from 2 to 10 ng/ml or else from 3 to 6 ng/ml, which is particularly important in the context of tests for detecting these bacteria by immunoassay.

The expression "maintaining the antigenic properties of the GDH" is intended to mean that the GDH retains its property of binding to the binding partners used in the context of the immunoassay since its structure is preserved, at least in terms of the antigenic determinant involved in the binding of the binding partner.

Of course, the prefix "immuno" in the term "immunoassay", for example, is not to be considered in the present application as strictly indicating that the binding partner is necessarily a partner of immunological origin, such as an antibody or an antibody fragment. Indeed, as is well known to those skilled in the art, this term is more widely used to denote tests and processes in which the binding partner is not a partner of immunological origin/nature, but consists, for example, of a receptor of the analyte that it is desired to detect and/or quantify. The requirement is that the binding partner concerned be capable of binding to the analyte being sought, preferably specifically. Thus, it is known practice to refer to the ELISA assay for assays which use binding partners that are not immunological in the strict sense, more widely known as "ligand binding assays", whereas the term "immuno" is included in the title in extenso corresponding to the acronym ELISA. In the interest of clarity and uniformity, the term "immuno" is used in the present application to denote any biological analysis using at least one binding partner suitable for binding to the analyte being sought and detecting and/or quantifying the latter, preferably specifically, even when said binding partner is not of immunological nature or origin in the strict sense.

The term "GDH binding partner" is intended to mean any molecule capable of binding to GDH. By way of example of a GDH binding partner, mention may be made of antibodies, antibody fragments, nanofitins, GDH receptors, aptamers, DARPins or any other molecule which is known to have an interaction with GDH.

The binding partner antibodies are, for example, either polyclonal antibodies or monoclonal antibodies.

The polyclonal antibodies can be obtained by immunization of an animal with the target GDH as immunogen, followed by recovery of the desired antibodies in purified form, by taking the serum of said animal, and separation of said antibodies from the other serum constituents, for example by affinity chromatography on a column to which is attached an antigen specifically recognized by the antibodies, in particular the immunogen, or by means of a protein A or G.

The monoclonal antibodies can be obtained by the hybridoma technique widely known to those skilled in the art. The monoclonal antibodies can also be recombinant antibodies obtained by genetic engineering, using techniques well known to those skilled in the art.

By way of example of antibody fragments, mention may be made of Fab, Fab', and F(ab')2 fragments and also scFvs (single chain variable fragments) and dsFvs (double-stranded variable fragments). These functional fragments can in particular be obtained by genetic engineering.

Nanofitins (commercial name) are small proteins which, like antibodies, are capable of binding to a biological target, thus making it possible to detect it, to capture it or quite simply to target it within an organism.

Aptamers are oligonucleotides, generally RNA or DNA, identified in libraries containing up to $10^{15}$ different sequences, by means of an in vitro combinatorial selection method known as SELEX for "Systematic Evolution of Ligands by Exponential Enrichment" (Ellington A D and Szostak J W., 1990). Most aptamers are composed of RNA, owing to the capacity of RNA to adopt varied and complex structures, thereby making it possible to create at its surface cavities of varied geometries, making it possible to bind various ligands. These are biochemical tools of interest which can be used in biotechnological, diagnostic or therapeutic applications. Their selectivity and their ligand-binding properties are comparable to those of antibodies.

"DARPins" for Designed Ankyrin Repeat ProteINS (Boersma Y L and Plackthun A, 2011) are another class of proteins which make it possible to mimic antibodies and to be able to bind to target proteins with high affinity and high selectivity. They derive from the family of ankyrin proteins, which are adapter proteins which enable the attachment of integral membrane proteins to the spectrin/actin network which constitutes the "backbone" of the cell plasma membrane. The structure of ankyrins is based on the repetition of a unit of approximately 33 amino acids and the same is true of DARPins. Each unit has a secondary structure of helix-turn-helix type. DARPins contain at least three, preferably four to five, repeat units and are obtained by screening combinatorial libraries.

The binding partners used may or may not be specific for GDH. They are termed specific when they are capable of binding exclusively or virtually exclusively to GDH. They are termed nonspecific when the GDH-binding selectivity is lower and they are then capable of binding to other ligands, such as other proteins or antibodies. According to one preferred embodiment, the specific binding partners are preferred.

The glutamate dehydrogenase that needs to be stabilized is any glutamate dehydrogenase from *Clostridium* of which it is desired to detect the presence, for example that of *Clostridium difficile*, of *Clostridium botulinum* or of *Clostridium perfringens*. It includes all the possible variants. Such proteins are known and their sequences are described for example in the Uniprot database (www.uniprot.org).

Thus, the GDH from *Clostridium difficile* (Uniprot accession no. P27346) is a protein of 421 amino acids, the reference amino acid sequence of which is the following SEQ ID NO 1:

```
         10         20         30         40
MSGKDVNVFE MAQSQVKNAC DKLGMEPAVY ELLKEPMRVI 50         60         70         80
EVSIPVKMDD GSIKTFKGFR SQHNDAVGPT KGGIRFHQNV 90        100        110        120
SRDEVKALSI WMTFKCSVTG IPYGGGKGGI IVDPSTLSQG 130        140        150        160
ELERLSRGYI DGIYKLIGEK VDVPAPDVNT NGQIMSWMVD 170        180        190        200
EYNKLTGQSS IGVITGKPVE FGGSLGRTAA TGFGVAVTAR 210        220        230        240
EAAAKLGIDM KKAKIAVQGI GNVGSYTVLN CEKLGGTVVA 250        260        270        280
MAEWCKSEGS YAIYNENGLD GQAMLDYMKE HGNLLNFPGA 290        300        310        320
KRISLEEFWA SDVDIVIPAA LENSITKEVA ESIKAKLVCE 330        340        350        360
AANGPTTPEA DEVFAERGIV LTPDILTNAG GVTVSYFEWV 370        380        390        400
QNLYGYYWSE EEVEQKEEIA MVKAFESIWK IKEEYNVTMR 410        420
EAAYMHSIKK VAEAMKLRGW Y
```

And the variants of which are:

TABLE 1

| Uniprot accession No. of the variants | Strain |
|---|---|
| Q18CS0 | *Clostridium difficile* (strain 630) |
| C9XIV3 | *Clostridium difficile* (strain CD196) |
| C9YHY9 | *Clostridium difficile* (strain R20291) |
| G6B2V9 | *Clostridium difficile* 002-P50-2011 |
| G6BHV4 | *Clostridium difficile* 050-P50-2011 |
| D5S4M2 | *Clostridium difficile* NAP07 |
| G6BQY2 | *Clostridium difficile* 70-100-2010 |
| D5Q9B1 | *Clostridium difficile* NAP08 |

The GDH from *Clostridium perfringens* is a protein which does not yet have a reference sequence in the Uniprot base. The first protein given in the Uniprot base (Uniprot accession No. Q8XK85) is the protein of strain 13/type A, of 448 amino acids, the amino acid sequence of which is the following SEQ ID NO 2:

```
         10         20         30         40
MEVKKYVDNL MEDLKKNNPG ESEFLAAAEE VLYSLVPVLE 50         60         70         80
KNPKYMEEGI LERIVEPERV IMFRVPWVDD AGNVRVNRGY 90        100        110        120
RVQFNSAIGP YKGGLRFHPS VNLSIIKFLG FEQIFKNSLT 130        140        150        160
TLPIGGGKGG SNFDPKGKSD REIMRFCQSF MSELYRHIGP 170        180        190        200
NTDVPAGDIG VGGREIGYMF GQYKKLKNSV DAGVLTGKGL 210        220        230        240
TYGGSLARKE ATGYGLVYFV DEMLRDNGQT IEGKTVVISG 250        260        270        280
SGNVAIYATE KVQELGGKVV ALSDSSGYVY DENGIDLEVV 290        300        310        320
KEIKEVKRGR ISEYVNYVKT AKFTEGFRGI WNVKCDIALP 330        340        350        360
CATQNEIDKS SAKTLIDNGV IAVGEGANMP STLEAQKLFV 370        380        390        400
DNKILFAPAK AANAGGVATS ALEMSQNSLR MSWTFEEVDA 410        420        430        440
KLKDIMKNIY YNSRNAASEY GHDGNLIVGA NIAGFKKVAD

AMLDHGII
```

And the variants of which are:

TABLE 2

| Uniprot accession No. of the variants | Strain |
|---|---|
| Q8XK85 | *Clostridium perfringens* (strain 13/Type A) |
| Q0SST9 | *Clostridium perfringens* (strain SM101/Type A) |
| Q0TQ84 | *Clostridium perfringens* (strain ATCC 13124/NCTC 8237/Type A) |
| B1R556 | *Clostridium perfringens* B str. ATCC 3626 |
| B1BJJ0 | *Clostridium perfringens* C str. JGS1495 |
| B1BWI0 | *Clostridium perfringens* E str. JGS1987 |
| B1RGN1 | *Clostridium perfringens* CPE str. F4969 |
| B1V119 | *Clostridium perfringens* D str. JGS1721 |

TABLE 2-continued

| Uniprot accession No. of the variants | Strain |
|---|---|
| B1RPY4 | *Clostridium perfringens* NCTC 8239 |
| H7CWP7 | *Clostridium perfringens* F262 |
| H1CRA8 | *Clostridium perfringens* WAL-14572 |

The GDH from *Clostridium botulinum* is a protein which does not yet have a reference sequence in the Uniprot base. The first protein given in the Uniprot base (Uniprot accession No. A5I2T3) is the protein of strain Hall/type A (ATCC 3502, NCTC 13319), of 421 amino acids, the amino acid sequence of which is the following SEQ ID NO 3:

```
         10         20         30         40
MAKENLNPFE NAQKQVKTAC DKLGMEPAVY ELLKEPQRVI 50         60         70         80
EVSIPVKMDD GSVKVFKGYR SQHNDAVGPT KGGVRFHPNV 90        100        110        120
SLDEVKALSI WMTFKCSVTG IPYGGGKGGI IVDPKTLSKG 130        140        150        160
ELERLSRGYI DGIHKLIGEK VDVPAPDVNT NGQIMAWMVD 170        180        190        200
EYNKLVGRSA IGVITGKPVE FGGSLGRNAA TGFGVAVTAR 210        220        230        240
EAAAKLGIDM KKAKLAIQGI GNVGSHTVLN CEKLGGTVVA 250        260        270        280
LAEWCKEEGT YAIYNENGLD GKAMIEYVKE NGNLLGYPGA 290        300        310        320
KKISLDEFWA LNVDILIPAA LENAITHENA SSINAKLVCE 330        340        350        360
AANGPITPDA DAILKEKGIT VTPDILTNAG GVTVSYFEWV 370        380        390        400
QNLYGYYWTE AEVEAKEEEA MVKAFESIWA IKEEYSVTMR 410        420
EAAYMHSIKK VAGAMKLRGW Y
```

And the variants of which, of 421, 447 or 450 amino acids according to the strains, are:

TABLE 3

| Uniprot accession No. of the variants | Strain |
|---|---|
| B1IM79 | *Clostridium botulinum* (strain Okra/Type B1)421 |
| B1KSB4 | *Clostridium botulinum* (strain Loch Maree/Type A3) |
| A7FUM1 | *Clostridium botulinum* (strain ATCC 19397/Type A) |
| E8ZRR3 | *Clostridium botulinum* (strain H04402 065/Type A5) |
| B2TLD1 | *Clostridium botulinum* (strain Eklund 17B/Type B) |
| C1FNV0 | *Clostridium botulinum* (strain Kyoto/Type A2) |
| B2V1W6 | *Clostridium botulinum* (strain Alaska E43/Type E3) |
| C3KX46 | *Clostridium botulinum* (strain 657/Type Ba4) |
| D5VZM8 | *Clostridium botulinum* (strain 230613/Type F) |
| F4A4K5 | *Clostridium botulinum* BKT015925 |
| A7GE56 | *Clostridium botulinum* (strain Langeland/NCTC 10281/Type F) |
| B1B9U1 | *Clostridium botulinum* C str. Eklund |
| C5VRL1 | *Clostridium botulinum* D str. 1873 |
| B1QDG7 | *Clostridium botulinum* NCTC 2916 |
| B1QQR1 | *Clostridium botulinum* Bf |
| M1ZQM8 | *Clostridium botulinum* CFSAN001627 |
| L1LK36 | *Clostridium botulinum* CFSAN001628 |
| C5UPY2 | *Clostridium botulinum* E1 str. 'BoNT E Beluga' |

According to one particular embodiment, the glutamate dehydrogenase is an enzyme from the bacterium of the species *Clostridium difficile*.

The glutamate dehydrogenase placed in an aqueous solution is either of natural origin, or of recombinant origin. The natural, or otherwise termed native, glutamate dehydrogenase can be obtained after culturing the *Clostridium* bacterium and purifying the protein from the bacterial lysate. The recombinant glutamate dehydrogenase can be obtained by genetic engineering, using techniques well known to those skilled in the art. Such obtaining is described, for example, by Anderson B M et al., 1993. The recombinant glutamate dehydrogenase can be obtained from companies such as Holzel Diagnostika GmbH (Germany).

The term "aqueous composition or solution" is intended to mean a clear liquid solution obtained by complete dissolution of one or more compounds and the major solvent of which is water, representing at least 50% by volume, generally at least 60%, 70%, 80% or 90%, relative to the total volume of the solution.

In the context of the present invention, the aqueous composition or solution is obtained by diluting the GDH in a solvent comprising predominantly water and a stabilizing compound as defined hereinafter. The stabilizing compound to be added to the aqueous solution containing the GDH to be stabilized is a carboxylic acid having a carbon-based chain of at least three carbon atoms and comprising at least two —COOH groups, or a salt thereof.

The expression "carboxylic acid having a carbon-based chain of at least three carbon atoms and comprising at least two —COOH groups" is intended to mean a molecule consisting of:
- a linear or branched carbon-based chain which is contiguous (i.e. without interruption in the carbon-based chain) or interrupted with at least one other atom other than a carbon atom, for example a nitrogen or oxygen atom,
- at least two —COOH groups at the chain end and
- at least one "CX" group, either at the chain end (it is then written —CX), or in the middle of the chain (it is then written —CX—), X being other than C.

For example, the —CX— groups are chosen independently from —CH$_2$—, =CH—, —C(H)OH—, —C(H)NH$_2$— and —C(O)—. The —CX groups are for their part chosen independently from —CH$_3$, —COOH (if there are more than two —COOH groups in the molecule) and —C(O)NH$_2$.

Thus, for example, the stabilizing compound may be succinic acid, of formula OH(O)C—(CH$_2$)$_2$—C(O)OH, which is a molecule having a contiguous linear carbon-based chain of four carbon atoms, two —COOH groups at the chain end and two —CH$_2$— groups.

Another example consists of fumaric acid of formula OH(O)C—(CH=CH)—C(O)OH, which is a molecule having a contiguous linear carbon-based chain of four carbon atoms, two —COOH groups at the chain end and two —CH— groups.

Yet another example consists of N-(2-acetamido)iminodiacetic acid, of formula H$_2$NC(O)—CH$_2$—N(CH$_2$—COOH)$_2$, which is a molecule having a branched carbon-based chain of six carbon atoms, interrupted with a nitrogen atom, consisting of two —COOH groups at the chain end, of three —CH$_2$— groups and of one —C(O)NH$_2$ group.

According to one particular embodiment, the stabilizing compound is chosen from: fumaric acid, succinic acid, malic acid, glutaric acid, citric acid, tartaric acid, N-(2-acetamido)

iminodiacetic acid, glutamic acid, adipic acid, aspartic acid, pimelic acid, malonic acid, and salts thereof, the formulae of which are given in FIG. 1.

The term "carboxylic acid salt" is intended to mean a salt of a monovalent cation. By way of monovalent cation, mention may be made of ammonium (NH4$^+$), silver (Ag$^+$), diamine silver (Ag(NH$_3$)$_2$$^+$), cesium (Cs$^+$), copper (I) (Cu$^+$), mercury (Hg$^+$), methanium (CH$_5$$^+$), methylium (CH$_3$$^+$) and nitrosium (NO$_2$$^+$) ions and ions of the alkali metals sodium (Na$^+$), potassium (K$^+$) and lithium (Li$^+$).

When the stabilizing compound is in salt form, at least one proton H$^+$ of the —COOH groups is replaced with a monovalent cation described above.

According to one preferred embodiment, the stabilizing compound is chosen from succinic acid, fumaric acid, and salts thereof, in particular alkali metal salts, as defined above.

The carbon-based chain may comprise one or more of the following characteristics:
  it may comprise at three carbon atoms to at most ten atoms, preferably at most eight, preferably at most seven, preferably at most six atoms,
  it intercalates a nitrogen atom or it is contiguous and consists only of carbon atoms,
  the "CX" groups are chosen independently from —CH$_2$—, =CH—, —CH$_3$, —COOH, —C(H)OH—, —C(O)NH$_2$, —C(H)NH$_2$— and —C(O)—, and
  it may or may not comprise one or more double bonds and the acid may then be in E or Z isomer form.

In particular, the carboxylic acid may have one or more of the following characteristics:
  a carbon-based chain of 4, 5 or 6 carbon atoms,
  a carbon-based chain of four carbon atoms having at least two —COOH groups and —CX— chosen independently from =CH—, —CH$_2$— and —C(H)OH—,
  a carbon-based chain of five carbon atoms having at least two —COOH groups and —CX— groups chosen from —CH$_2$— and —C(H)NH$_2$—,
  a carbon-based chain of six carbon atoms having at least two —COOH groups and "CX" groups chosen from —CH$_2$—, —C(H)OH—(—CX—) and —C(O)NH$_2$ (—CX),
  one double bond and is an E isomer,
  two —COOH groups.

The amount of GDH present in the aqueous solution depends on the final use of the aqueous composition which contains it. In the context of a conventional immunoassay, the GDH may be present in a proportion of from 0.75 to 10 ng/ml, or from 2 to 10 ng/ml, preferably from 3 to 6 ng/ml. In the context of an "ultrasensitive" immunoassay, the GDH will be present in a much lower amount, for example less than one pg/ml, or even about one fg/ml.

The amount of stabilizing compound to be added to the aqueous solution containing the GDH is in large excess relative to the amount of GDH. It depends on whether the stabilizing compound is used only as a stabilizing compound, another molecule then being added as a buffer, or else whether it is used both as a stabilizing compound and as a buffer. Thus, for example, when the stabilizing compound is only used as a stabilizing compound, from 20 to 100 molecules of stabilizing compound are added per GDH monomer, preferably from 30 to 80 molecules of stabilizing compound per GDH monomer, more preferably from 40 to 60 molecules of stabilizing compound per GDH monomer. In this case, the compound added as a buffer is any compound known to those skilled in the art having a pH of between 4.5 and 7, preferably between 5.5 and 6.5, a pH of 5.8 being preferred. By way of example of a compound added as a buffer, mention may be made of phosphate and acetate. When the stabilizing compound is used both as a stabilizing compound and as a buffer, from $10^8$ to $10^{10}$ molecules of stabilizing compound are added per GDH monomer, preferably from $1\times10^9$ to $5\times10^9$ molecules of stabilizing compound per GDH monomer, more preferably from $1\times10^9$ to $2\times10^9$ molecules of stabilizing compound per GDH monomer.

Other compounds may also be added to the aqueous composition in the process of the invention. Thus, for example, a polyol may be added. The addition of polyol makes it possible to promote the heat stability of the proteins (resistance to heat denaturation) and also to prevent aggregation. Generally, polyols have a co-solvent effect and contribute to maintaining the native conformation of proteins in an aqueous solution.

By way of examples of polyol, mention may be made of monosaccharide polyols such as triols, for example glycerol, tetraols, for example erythritol, pentols, for example xylitol, arabitol and ribitol, hexols, for example sorbitol, dulcitol and mannitol, heptols, for example volemitol, and also disaccharide polyols such as maltitol, isomaltitol and lactitol.

According to one embodiment of the invention, the polyol added to the aqueous composition of the process of the invention is sorbitol.

The polyol is added to the aqueous composition in a proportion of at least 1%, preferably at least 5% and more preferably at least 10%, with at most 50%.

The composition may also comprise another macro molecule, generically referred to as a "filler protein" even though macromolecules other than proteins are appropriate, which has nothing to do with the GDH, but is present in large excess relative to the GDH, further improving the stabilization of the GDH. This "filler protein" has a shield effect in the sense that it will partially undergo physico-chemical modifications in the aqueous solution, thus making it possible to protect the molecule of interest, in this case GDH. This added macromolecule may for example be a protein such as BSA (bovine serum albumin), or else synthetic polymers of dextran or polyethylene glycol type. BSA, for example, is added in a proportion of 50 g/l compared with 3 mg/l of GDH.

The aqueous composition is buffered so as to have a pH of between 4.5 and 7, preferably between 5.5 and 6.5, a pH of 5.8 being preferred. As previously indicated, the stabilizing compound of the invention may also be used as a buffer, or else another buffer compound may be added.

The aqueous compositions comprising the glutamate dehydrogenase from a bacterium of the *Clostridium* genus and a stabilizing compound which is a carboxylic acid having a carbon-based chain of at least three carbon atoms and comprising at least two —COOH groups, or a salt thereof, it being understood that the stabilizing compound is neither glutamate, nor alpha-ketoglutarate, produced from hydrolysis of the glutamate by the GDH enzyme and the NAD+ coenzyme, nor citrate, nor succinate, nor glutarate, are novel and constitute another subject of the invention.

According to another embodiment, the aqueous compositions of the invention also exclude glutamic acid, alpha-ketoglutaric acid, glutaric acid, succinic acid and/or citric acid.

When the bacterium of the *Clostridium* genus is chosen from the species *Clostridium difficile, Clostridium botulinum* and *Clostridium perfringens*, then the aqueous compositions comprising the glutamate dehydrogenase from one of these bacteria and a stabilizing compound which is a carboxylic acid having a carbon-based chain of at least three carbon atoms and comprising at least two —COOH groups, or a salt thereof, it being understood that the stabilizing compound is neither glutamate, nor alpha-ketoglutarate, nor citrate, are novel and constitute another subject of the invention.

According to another embodiment, the aqueous compositions of the invention also exclude glutamic acid, alpha-ketoglutaric acid and/or citric acid.

The same characteristics and preferences described previously, in particular with regard to the choice of the GDH, of the stabilizing compound, of the compounds to be added and of the relative amount thereof, given in relation to the process, also apply to the aqueous compositions according to the invention.

The aqueous compositions of the invention, in particular those obtained according to the process of the invention, are particularly useful for detecting the presence of a bacterium of the *Clostridium* genus in a biological sample that may contain such a bacterium. Thus, the kits containing such compositions constitute another subject of the invention.

The biological samples that may contain a bacterium of the *Clostridium* genus may be samples from the clinical field or from the field of testing innocuity, or even sterility of industrial products. In the clinical field, the sample is an animal, preferably human, biological specimen, such as stools or derivatives, for example an extract of fecal proteins, urine, blood or derivatives, for example serum or plasma, pus, etc. In the industrial field, the sample comes from a food or cosmetic product.

The kits according to the invention may also contain the compounds required for carrying out a process for detecting, for example by immunoassay, the presence of a bacterium of the *Clostridium* genus, and in particular *Clostridium difficile*. Thus, for example, the kits may contain one or more GDH-binding partners as previously described, and all the compounds required for demonstrating the reaction between the binding partner(s) and the GDH.

The qualitative or quantitative GDH immunological assay will preferably be a sandwich assay, which is an assay widely known to those skilled in the art using two GDH-binding partners. One of the two partners may be coupled to a label so as to form a conjugate or a tracer. The other binding partner may be captured on a solid support. The term "capture partner" is then used for the latter and detection partner is then used for the former.

The measured signal emitted by the conjugate is then proportional to the amount of GDH in the biological sample.

The term "label" is intended to mean in particular any molecule containing a group that reacts with a group of the binding partner, directly without chemical modification, or after chemical modification so as to include such a group, which molecule is capable of directly or indirectly generating a detectable signal. A nonlimiting list of these direct detection labels consists of:

enzymes which produce a detectable signal for example by colorimetry, fluorescence, luminescence, such as horseradish peroxydase, alkaline phosphatase, β-galactosidase or glucose-6-phosphate dehydrogenase,
chromophores such as fluorescent, luminescent or dye compounds,
radioactive molecules such as $^{32}P$, $^{35}S$ or $^{125}I$,
fluorescent molecules such as Alexas or phycocyanins, and
electrochemiluminescent salts such as organometallic derivatives based on acridinium or on ruthenium.

Indirect detection systems may also be used, for instance ligands capable of reacting with an anti-ligand. The ligand then corresponds to the label so as to constitute, with the binding partner, the conjugate.

Ligand/anti-ligand pairs are well known to those skilled in the art, which is the case, for example, of the following pairs: biotin/streptavidin, hapten/antibody, antigen/antibody, peptide/antibody, sugar/lectin, polynucleotide/polynucleotide complementary to said polynucleotide.

The anti-ligand may then be directly detectable by the direct detection labels previously described or be itself detectable by another ligand/anti-ligand pair, and so on.

These indirect detection systems may result, under certain conditions, in an amplification of the signal. This signal amplification technique is well known to those skilled in the art, and reference may be made to the applicant's prior patent applications FR 2781802 or WO 95/08000.

Depending on the type of labeling used, those skilled in the art will add reagents which allow the visualization of the labeling or the emission of a signal detectable by any type of appropriate measuring apparatus, for instance a spectrophotometer, a spectrofluorimeter, a densitometer or else a high-definition camera.

In the GDH assay processes, aqueous compositions of the invention, where appropriate obtained according to the process of the invention, are particularly useful for establishing a standard range, this constituting another subject of the invention. The establishing of the standard range, a step that is necessary in order to be able to quantify the GDH, is a step widely known to those skilled in the art. Briefly, it consists in measuring the signal generated by increasing and known amounts or concentrations of the GDH analyte, in plotting the curve giving the signal as a function of the amount or the concentration and in finding a mathematical model which represents this relationship in the most faithful way possible. To do this, several aqueous compositions of the invention are used, each containing a different GDH concentration. The mathematical model will be used to determine by extrapolation the unknown amounts or concentrations of GDH contained in the biological sample to be tested.

The aqueous compositions of the invention, where appropriate obtained according to the process of the invention, are also particularly useful as a calibrator, which constitutes another subject of the invention. In this case, the GDH concentration of the composition is fixed and known. The signal generated during the use of the immunoassay kit by the calibrator is also known. The calibrator is used to verify that the measurement (signal) produced during the use of the immunoassay kit indeed corresponds to the expected value. If this is not the case, the calibrator is used to measure the shift which may, where appropriate, be corrected mathematically or by a physical intervention on the measuring instrument (adjustment).

The aqueous compositions of the invention, where appropriate obtained according to the process of the invention, are also particularly useful as a control, which constitutes another subject of the invention. In this respect, they are used, for example, to verify that the immunoassay kit operates according to expectations (also called positive control) and that the detection of the GDH in the biological sample is not falsely negative in so far as the detection method has operated correctly with the aqueous composition of the invention.

The detection of GDH in a biological sample makes it possible to conclude that the bacterium is present.

Thus, another subject of the invention relates to a process for detecting the presence of a bacterium of the *Clostridium* genus in a biological sample that may contain such a bacterium, characterized in that it comprises the steps of (i) carrying out a process for detecting the presence of a bacterium of the *Clostridium* genus by detecting or quantifying glutamate dehydrogenase in said sample using an aqueous composition of the invention, where appropriate as obtained according to the process of the invention, or else a kit as previously defined, and (ii) if the process of step (i) is positive, concluding that the bacterium is present.

In other words, for step (ii), a positive result in step (i) makes it possible to conclude that the bacterium is present.

On the other hand, this provides no information as to whether or not this bacterium produces at least one toxin, which is particularly important as an aid to diagnosis when a patient presents symptoms that might be caused by the presence of a bacterium which is toxigenic and which expresses at least one toxin.

Thus, another subject of the invention relates to a process for detecting the presence of a toxigenic bacterium of the *Clostridium* genus which produces at least one toxin, in a biological sample that may contain such a bacterium and at least one such toxin, characterized in that it comprises the steps of:

(i) carrying out a process for detecting the presence of a bacterium of the *Clostridium* genus by detecting or quantifying glutamate dehydrogenase in said sample using an aqueous composition of the invention, where appropriate as obtained according to the process of the invention, or else a kit as previously defined, and (ii) if the process of step (i) is negative, concluding that the bacterium is absent, or (ii') if the process of step (i) is positive, carrying out a process for detecting or quantifying at least one toxin that may be released by said bacterium of the *Clostridium* genus, in the same biological sample, or in a new biological sample from the same individual, and concluding that the bacterium is toxigenic and produces said at least one toxin if said at least one toxin is present.

In other words, for step (ii), a negative result in step (i) makes it possible to conclude that the bacterium is absent and a positive result in step (i) makes it possible to conclude that the bacterium is present.

Step (i) above consisting in detecting the presence of a bacterium of the *Clostridium* genus by detecting or quantifying glutamate dehydrogenase in the biological sample has been described previously. The aqueous composition of the invention, where appropriate obtained by means of the process of the invention, can then be used to produce the standard range and/or as a calibrator and/or as a positive control.

Step (ii') above consisting in detecting or quantifying at least one toxin that may be released by said bacterium of the *Clostridium* genus is a step widely known to those skilled in the art. Such detecting or quantifying may be carried out, for example, by immunoassay using partners for binding to the toxins being sought. The toxin immunoassay is carried out in a manner similar to the GDH immunoassay as described previously. Kits for immunoassaying toxin from bacteria of the *Clostridium* genus are commercially available, for instance the VIDAS® *Clostridium difficile* A&B kit which makes it possible to detect *Clostridium difficile* toxins A and B.

Mass spectrometry may also be used to carry out the step of detecting/quantifying the toxin. This technique is an analytical technique which makes it possible to determine the molar mass of the compounds analyzed, and also to identify their molecular structure, or even to quantify them. Applied to a complex mixture such as a biological fluid or stools, it needs to be coupled to a separative technique which makes it possible to reduce the complexity thereof. This is usually gas chromatography (GC) or liquid chromatography (LC). Tandem mass spectrometry (MS/MS) combines two analyzers and may be used for the purposes of detection/quantification. The ionic compounds selected in the first analyzer and then fragmented are analyzed more finely in the second. This double analysis makes it possible to significantly increase the specificity of the method. For this technology, reference may in particular be made to Van den Broek et al., 2013.

The detecting and/or quantifying of the toxins may also be carried out by means of a test for immunotoxicity in the stools (CTA) which makes it possible to demonstrate the biological effects of toxins in the stools (Eckert C. et al., 2011).

The detecting or quantifying of the toxin is carried out in the same biological sample as that used for detecting or quantifying the GDH, a part of which has been kept in this respect, or else in a new biological sample from the same origin, i.e. from the individual from whom the first biological sample tested with respect to the presence of GDH came if the biological sample is a clinical sample or from the same source if the biological sample is an industrial sample. The second biological sample is either of the same nature, or of different nature, the first case being preferred.

According to one particular embodiment, the toxigenic bacterium of which it is desired to detect the presence is *Clostridium difficile* and said at least one toxin comprises toxin A, toxin B or both.

Other toxigenic bacteria of the *Clostridium* genus have been described previously.

Figure 2:
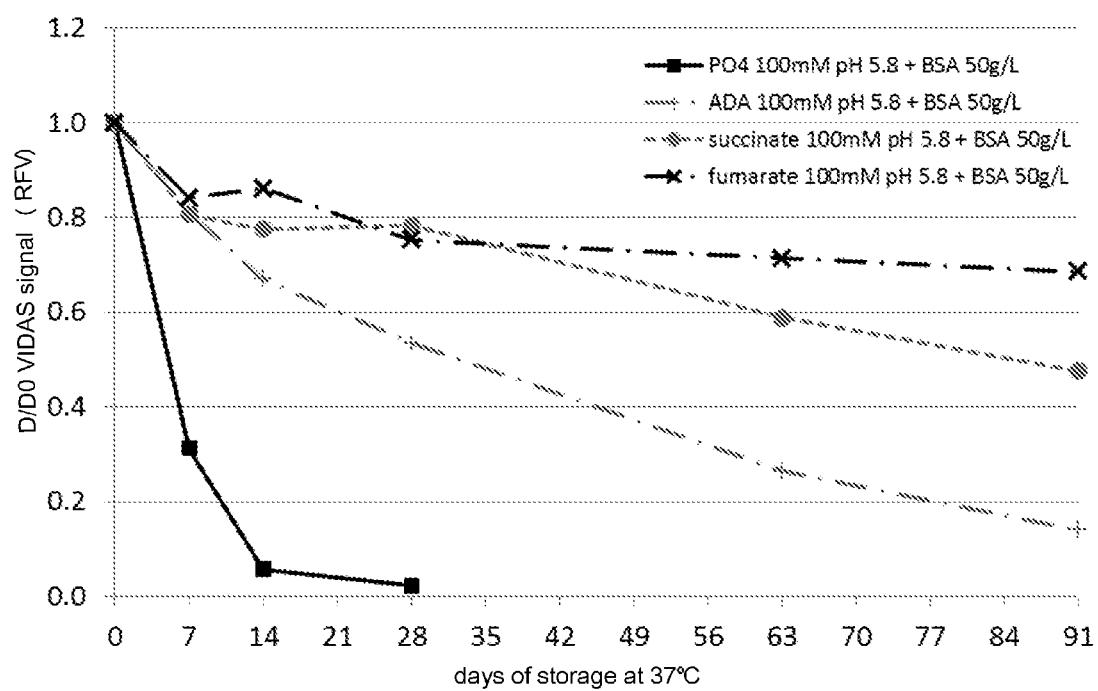

The invention will be understood more clearly by means of the following examples which are given by way of nonlimiting illustration, and also by means of FIGS. 1 and 2, in which:

FIG. 1 gives examples of stabilizing compounds used in the aqueous compositions according to the invention, and also the chemical formula thereof, and FIG. 2 is a graph giving the change in the fluorescent signal obtained during an immunoassay with the VIDAS® GDH kit (bioMérieux) emitted by aqueous compositions according to the invention or comparative compositions, as a function of time, when these compositions are maintained at 37° C.

EXAMPLES

Example 1: Preparation of Recombinant GDH from *Clostridium difficile*

The gluD gene encoding the GDH from *Clostridium difficile* (Genbank accession No. M65250), with a sequencing encoding a HIS tag added thereto, is cloned into the pMR78 vector (bioMérieux, France). The expression plasmid thus constructed is introduced into *E. coli* BL21 bacteria and derivatives (Stratagene, Agilent Technologies). The cultures are carried out in 2×YT medium (Difco), in the presence of ampicillin, at 37° C. with shaking. The expression of the protein is induced by adding 1 mM of IPTG (isopropyl beta-D-1-thiogalactopyranoside). The bacteria are collected by centrifugation at the end of culturing.

The bacterial pellets are taken up in 2×PBS buffer (phosphate buffered saline) and lysed. The lysates are centrifuged at 3000 g for 30 min at 4° C. The supernatant contains the soluble proteins, including the recombinant GDH to be purified.

The purification of the protein is carried out by one-step metal chelate affinity chromatography. The supernatant obtained after centrifugation is loaded onto an Ni-NTA-Agarose resin (Qiagen). After a washing cycle, the protein is eluted in the presence of an imidazol gradient. The protein is dialyzed in a 20 mM phosphate buffer.

Example 2: Demonstration of the Stabilization of the Antigenic Properties of GDH Using Stabilizing Compounds According to the Invention The recombinant GDH, prepared in example 1, is diluted to 3 ng/ml in the following formulations, according to the indications relating to the calibrator and control (S1/C1) given in the information sheet for the VIDAS® GDH reagent (Ref 30125, bioMérieux, France):
Comparative composition: 100 mM phosphate+50 g/l BSA, pH 5.8 (formulation of the calibration solution of the Vidas® kit, GDH in lyophilized form, taken up in demineralized water),
Composition according to the invention 1:100 mM N-(2-acetamido)iminodiacetic acid (ADA)+50 g/l BSA, pH 5.8 (ADA composition),
Composition according to the invention 2:100 mM succinic acid+50 g/l BSA, pH 5.8 (succinate composition),
Composition according to the invention 3:100 mM disodium fumarate+50 g/l BSA, pH 5.8 (fumarate composition).

Each composition (comparative and ADA, succinate and fumarate) was prepared beforehand as follows: each stabilizing compound (1.18 g of succinic acid —Merck, 1.6 g of dibasic sodium fumarate—Sigma, 1.90 g of ADA—Sigma or 0.78 g of phosphate NaH$_2$PO$_4$.2H$_2$O+1.79 g of Na$_2$HPO$_4$.12H$_2$O) was mixed with demineralized water so as to obtain 50 ml. 10 N NaOH was then added so as to adjust the pH to 5.8. Five g of BSA (Millipore) were added. Finally, demineralized water was added to as to obtain a solution of 100 ml.

The four compositions containing the GDH are then aliquoted into fractions of 1 ml and then stored at 37+/−1° C. The impact of the formulation on the stability of the antigenic properties of the recombinant GDH protein is evaluated by carrying out several GDH assays over a period of 91 days with the VIDAS® GDH kit (Ref 30125) and the VIDAS® instrument according to the instructions of the manufacturer (bioMérieux, France).

The implementation of the VIDAS GDH test adheres to the protocol of the kit sold:
introduction of 200 μl of sample+1 ml of the R1 pretreatment reagent
homogenization by vortexing
introduction of 300 μl of this dilution to ⅙ into the sample well of the cartridge of the VIDAS® GDH kit.

Each aliquot is used for only one monitoring timepoint, but is systematically used in duplicate. The VIDAS instrument measures a fluorescence signal and the results are expressed as "relative fluorescence value" or RFV.

The RFV results obtained for the two measurements in duplicate (1 and 2) and also the D/D0 ratio (RFV on day D relative to RFV on day 0) are given in table 4 below and are also reproduced on the graph of FIG. 2.

TABLE 4

| Days 37° C. | Comparative composition | | | ADA composition | | | Succinate composition | | | Fumarate composition | | |
|---|---|---|---|---|---|---|---|---|---|---|---|---|
| | 1 | 2 | D/D0 | 1 | 2 | D/D0 | 1 | 2 | D/D0 | 1 | 2 | D/D0 |
| 0 | 417 | 445 | 1 | 428 | 451 | 1 | 419 | 462 | 1 | 446 | 428 | 1 |
| 7 | 132 | 137 | 0.31 | 355 | 357 | 0.81 | 339 | 371 | 0.81 | 371 | 364 | 0.84 |
| 14 | 25 | 25 | 0.06 | 278 | 311 | 0.67 | 343 | 340 | 0.78 | 375 | 378 | 0.86 |
| 28 | 8 | 12 | 0.02 | 249 | 221 | 0.53 | 336 | 354 | 0.78 | 329 | 329 | 0.75 |
| 63 | NA | NA | NA | 124 | 108 | 0.26 | 258 | 260 | 0.59 | 322 | 302 | 0.71 |
| 91 | NA | NA | NA | 59 | 64 | 0.14 | 209 | 210 | 0.48 | 297 | 302 | 0.69 |

NA = not applicable

The results demonstrate that, at 37° C., the use of stabilizing compounds consisting of carboxylic acids having a carbon-based chain of at least three carbon atoms and comprising at least two —COOH groups makes it possible to very substantially improve the storage time of an aqueous solution containing GDH since, for the comparative composition, there is no longer any signal at 28 days, whereas the D/D0 ratio at this date for the compositions according to the invention is at least equal to 0.5.

Example 3: Monitoring of the Antigenic Properties of GDH in an Aqueous Solution Using Citric Acid as Stabilizing Compound The procedure of example 2 was repeated, except for the fact that citric acid (100 mM) was used as stabilizing compound and that the aqueous solutions were stored for a longer period of time, at 2-8° C. and at 37° C.

The RFV results obtained for the two measurements in duplicate (1 and 2) and also the D/D0 ratio are given in table 5 below.

TABLE 5

| | Citrate composition-37° C. | | | Citrate composition-2-8° C. | | |
|---|---|---|---|---|---|---|
| Days | 1 | 2 | D/D0 | 1 | 2 | D/D0 |
| 0 | 713 | 677 | 1 | 713 | 677 | 1 |
| 1 | 697 | 757 | 1.05 | 653 | 722 | 0.99 |
| 7 | 717 | 683 | 1 | 636 | 694 | 0.96 |
| 14 | 666 | 678 | 0.97 | 646 | 700 | 0.97 |
| 29 | 521 | 565 | 0.78 | 692 | 680 | 0.99 |
| 51 | 421 | 418 | 0.6 | 613 | 641 | 0.9 |
| 78 | 233 | 222 | 0.33 | 701 | 680 | 0.99 |
| 124 | 67 | 67 | 0.1 | 648 | 690 | 0.96 |
| 184 | 6 | 10 | 0.01 | 739 | 774 | 1.09 |
| 275 | NA | NA | NA | 657 | 663 | 0.95 |
| 369 | NA | NA | NA | 664 | 612 | 0.92 |
| 552 | NA | NA | NA | 523 | 558 | 0.78 |

NA: not applicable

The above results demonstrate that the addition of citric acid allows very good stability associated with the preservation of the antigenic properties of the GDH, with a virtually optimal stabilization, even after 18 months, when the aqueous composition is stored between 2-8° C.

Example 4: Monitoring of the Antigenic Properties of GDH in an Aqueous Solution Using Succinic Acid and Sorbitol The procedure of example 2 was repeated, except for the fact that 10% of sorbitol was also added to a succinate composition and that the aqueous solutions were stored for a longer period of time, at 2-8° C. and at 37° C.

The RFV results obtained for the two measurements in duplicate (1 and 2) and also the D/D0 ratio are given in table 6 below.

TABLE 6

| | Succinate composition with sorbitol-37° C. | | | Succinate composition with sorbitol-2-8° C. | | |
|---|---|---|---|---|---|---|
| Days | 1 | 2 | D/D0 | 1 | 2 | D/D0 |
| 0 | 726 | 710 | 1 | 726 | 710 | 1 |
| 1 | 740 | 714 | 1 | 744 | 700 | 1.01 |
| 7 | 702 | 696 | 0.97 | 725 | 764 | 1.04 |
| 14 | 689 | 655 | 0.94 | 720 | 765 | 1.03 |
| 29 | 624 | 658 | 0.89 | 690 | 708 | 0.97 |
| 51 | 653 | 646 | 0.9 | 603 | 668 | 0.89 |
| 78 | 606 | 591 | 0.83 | 670 | 720 | 0.97 |
| 124 | 529 | 556 | 0.76 | 709 | 691 | 0.97 |
| 184 | 379 | 376 | 0.53 | 656 | 785 | 1 |
| 275 | 267 | 286 | 0.39 | 659 | 710 | 0.95 |
| 369 | 156 | 161 | 0.22 | 692 | 663 | 0.94 |
| 552 | 48 | 48 | 0.07 | 663 | 710 | 0.96 |
| 891 | NC | NC | NC | 638 | 681 | 0.92 |

NC: not calculated

The above results demonstrate that succinic acid also allows a lengthy stabilization of the antigenic properties of the GDH in an aqueous solution, the addition of sorbitol not modifying this stabilization, with a stabilization which is virtually optimal, even after approximately 30 months, when the aqueous solution is stored between 2-8° C.

LITERATURE REFERENCES

Anderson B M et al, 1993, Archives of Biochemistry and Biophysics, 300(1): 483-488

Boersma Y L, Plückthun A, 2011, Curr. Opin. Biotechnol, 22: 849-857

Eckert C. et al., 2011, Journal des Anti-Infectieux, 13(2): 109-116

Ellington A D et Szostak J W., 1990, Nature, 346: 818-822

Garcia-Galan C. et al., 2013, Enzyme and Microbial Technology, 52(4-5): 211-217

Van den Broek et al., 2013, J. Chromatogr. B, 929: 161-179

The invention claimed is:

1. A process for stabilizing glutamate dehydrogenase from a bacterium of the *Clostridium* genus in order to maintain antigenic properties of the glutamate dehydrogenase, comprising:
stabilizing the glutamate dehydrogenase in an aqueous solution comprising (i) a stabilizing compound that is a carboxylic acid having a carbon-based chain of at least three carbon atoms and comprising at least two —COOH groups, or a salt thereof, and (ii) any of a monosaccharide polyol, disaccharide polyol, or polymeric macromolecule in addition to the glutamate dehydrogenase; and
maintaining the antigenic properties of the glutamate dehydrogenase during storage of the aqueous solution, wherein:
the glutamate dehydrogenase is in the aqueous solution at a concentration ranging from 0.75 to 10 ng/ml; and
the aqueous composition has a pH of between 4.5 and 7.

2. The process as claimed in claim 1, wherein the carboxylic acid contains a carbon-based chain of 4, 5 or 6 carbon atoms.

3. The process as claimed in claim 1, wherein the stabilizing compound is chosen from the following carboxylic acids and salts thereof:
  (i) carboxylic acids containing a carbon-based chain of four carbon atoms having at least two —COOH groups and —CX— groups chosen independently from =CH—, —CH$_2$— and —C(H)OH—, and
  (ii) carboxylic acids containing a carbon-based chain of five carbon atoms having at least two —COOH groups and "CX" groups chosen from —CH$_2$— and —C(H)NH$_2$—, and
  (iii) carboxylic acids containing a carbon-based chain of six carbon atoms having at least two —COOH groups and "CX" groups chosen from —CH$_2$—, —C(H)OH— and —C(O)NH$_2$.

4. The process as claimed in claim 1, wherein the carboxylic acid contains a double bond in its carbon-based chain and is an E isomer.

5. The process as claimed in claim 1, wherein the carboxylic acid contains two —COOH groups.

6. The process as claimed in claim 1, wherein the stabilizing compound is chosen from fumaric acid, succinic acid, malic acid, glutaric acid, citric acid, tartaric acid, N-(2-acetamido)iminodiacetic acid, glutamic acid, adipic acid, aspartic acid, pimelic acid and malonic acid, and salts thereof.

7. The process as claimed in claim 1, wherein the stabilizing compound is chosen from succinic acid and fumaric acid, and salts thereof.

8. The process as claimed in claim 1, wherein the stabilizing compound is chosen from malic acid, glutaric acid, citric acid, N-(2-acetamido)iminodiacetic acid, glutamic acid, adipic acid, pimelic acid and malonic acid, and salts thereof.

9. The process as claimed in claim 1, wherein the aqueous solution comprises at least 50% by volume of water.

10. The process as claimed in claim 1, wherein the aqueous solution comprises any of glycerol, erythritol, xylitol, arabitol, ribitol, sorbitol, dulcitol, mannitol, or volemitol as the monosaccharide polyol.

11. The process as claimed in claim 1, wherein the aqueous solution comprises any of maltitol, isomaltitol, or lactitol as the disaccharide polyol.

12. The process as claimed in claim 1, wherein the aqueous solution comprises a filler protein as the polymeric macromolecule.

13. The process as claimed in claim 1, wherein the aqueous solution comprises a dextran or polyethylene glycol polymer as the polymeric macromolecule.

14. The process as claimed in claim 1, further comprising binding a binding partner to the glutamate dehydrogenase to detect or quantify the glutamate dehydrogenase as part of a glutamate dehydrogenase immunoassay.

15. The process as claimed in claim 14, wherein the glutamate dehydrogenase is detected or quantified as a control, a calibrator, or for establishing a standard concentration range.

16. An aqueous composition comprising:
  (i) glutamate dehydrogenase from a bacterium of the *Clostridium* genus;
  (ii) a stabilizing compound that is a carboxylic acid having a carbon-based chain of at least three carbon atoms and comprising at least two —COOH groups, or a salt thereof; and
  (iii) any of a monosaccharide polyol, disaccharide polyol, or polymeric macromolecule in addition to the glutamate dehydrogenase, wherein:
    the glutamate dehydrogenase is in the aqueous composition at a concentration ranging from 0.75 to 10 ng/ml; and
    the aqueous composition has a pH of between 4.5 and 7.

17. A kit for detecting the presence of a bacterium of the *Clostridium* genus in a biological sample that may contain the bacterium, comprising the aqueous composition as claimed in claim 16 and compounds required for carrying out a process for detecting the presence of the bacterium of the *Clostridium* genus.

18. The aqueous composition as claimed in claim 16, wherein the carboxylic acid contains a carbon-based chain of 4, 5 or 6 carbon atoms.

19. The aqueous composition as claimed in claim 16, wherein the stabilizing compound is chosen from the following carboxylic acids and salts thereof:
  (i) carboxylic acids containing a carbon-based chain of four carbon atoms having at least two —COOH groups and —CX— groups chosen independently from =CH—, —CH$_2$— and —C(H)OH—, and
  (ii) carboxylic acids containing a carbon-based chain of five carbon atoms having at least two —COOH groups and —CX— groups chosen from —CH$_2$— and —C(H)NH$_2$—, and
  (iii) carboxylic acids containing a carbon-based chain of six carbon atoms having at least two —COOH groups and "CX" groups chosen from —CH$_2$—, —C(H)OH— and —C(O)NH$_2$.

20. The aqueous composition as claimed in claim 16, wherein the carboxylic acid contains a double bond in its carbon-based chain and is an E isomer.

21. The aqueous composition as claimed in claim 16, wherein the carboxylic acid contains two —COOH groups.

22. The aqueous composition as claimed in claim 16, wherein the stabilizing compound is chosen from fumaric acid, succinic acid, malic acid, glutaric acid, citric acid, tartaric acid, N-(2-acetamido)iminodiacetic acid, glutamic acid, adipic acid, aspartic acid, pimelic acid and malonic acid, and salts thereof.

23. The aqueous composition as claimed in claim 16, wherein the stabilizing compound is chosen from succinic acid and fumaric acid, and salts thereof.

24. The aqueous composition as claimed in claim 16, wherein the stabilizing compound is chosen from malic acid, glutaric acid, citric acid, N-(2-acetamido)iminodiacetic acid, glutamic acid, adipic acid, pimelic acid and malonic acid, and salts thereof.

25. The aqueous composition as claimed in claim 16, comprising at least 50% by volume of water.

26. The aqueous composition as claimed in claim 16, comprising any of glycerol, erythritol, xylitol, arabitol, ribitol, sorbitol, dulcitol, mannitol, or volemitol as the monosaccharide polyol.

27. The aqueous composition as claimed in claim 16, comprising any of maltitol, isomaltitol, or lactitol as the disaccharide polyol.

28. The aqueous composition as claimed in claim 16, comprising a filler protein as the polymeric macromolecule.

29. The aqueous composition as claimed in claim 16, comprising a dextran or polyethylene glycol polymer as the polymeric macromolecule.

* * * * *

SEQUENCE LISTING

```
<160> NUMBER OF SEQ ID NOS: 3

<210> SEQ ID NO 1
<211> LENGTH: 421
<212> TYPE: PRT
<213> ORGANISM: Clostridium difficile

<400> SEQUENCE: 1

Met Ser Gly Lys Asp Val Asn Val Phe Glu Met Ala Gln Ser Gln Val
1               5                   10                  15

Lys Asn Ala Cys Asp Lys Leu Gly Met Glu Pro Ala Val Tyr Glu Leu
            20                  25                  30

Leu Lys Glu Pro Met Arg Val Ile Glu Val Ser Ile Pro Val Lys Met
        35                  40                  45

Asp Asp Gly Ser Ile Lys Thr Phe Lys Gly Phe Arg Ser Gln His Asn
    50                  55                  60

Asp Ala Val Gly Pro Thr Lys Gly Gly Ile Arg Phe His Gln Asn Val
65                  70                  75                  80

Ser Arg Asp Glu Val Lys Ala Leu Ser Ile Trp Met Thr Phe Lys Cys
                85                  90                  95

Ser Val Thr Gly Ile Pro Tyr Gly Gly Gly Lys Gly Gly Ile Ile Val
            100                 105                 110

Asp Pro Ser Thr Leu Ser Gln Gly Glu Leu Glu Arg Leu Ser Arg Gly
        115                 120                 125

Tyr Ile Asp Gly Ile Tyr Lys Leu Ile Gly Glu Lys Val Asp Val Pro
    130                 135                 140

Ala Pro Asp Val Asn Thr Asn Gly Gln Ile Met Ser Trp Met Val Asp
145                 150                 155                 160

Glu Tyr Asn Lys Leu Thr Gly Gln Ser Ser Ile Gly Val Ile Thr Gly
                165                 170                 175

Lys Pro Val Glu Phe Gly Gly Ser Leu Gly Arg Thr Ala Ala Thr Gly
            180                 185                 190

Phe Gly Val Ala Val Thr Ala Arg Glu Ala Ala Ala Lys Leu Gly Ile
        195                 200                 205

Asp Met Lys Lys Ala Lys Ile Ala Val Gln Gly Ile Gly Asn Val Gly
```

```
            210                 215                 220
Ser Tyr Thr Val Leu Asn Cys Glu Lys Leu Gly Gly Thr Val Ala
225                 230                 235                 240

Met Ala Glu Trp Cys Lys Ser Glu Gly Ser Tyr Ala Ile Tyr Asn Glu
                    245                 250                 255

Asn Gly Leu Asp Gly Gln Ala Met Leu Asp Tyr Met Lys Glu His Gly
                260                 265                 270

Asn Leu Leu Asn Phe Pro Gly Ala Lys Arg Ile Ser Leu Glu Glu Phe
            275                 280                 285

Trp Ala Ser Asp Val Asp Ile Val Pro Ala Ala Leu Glu Asn Ser
    290                 295                 300

Ile Thr Lys Glu Val Ala Glu Ser Ile Lys Ala Lys Leu Val Cys Glu
305                 310                 315                 320

Ala Ala Asn Gly Pro Thr Thr Pro Glu Ala Asp Glu Val Phe Ala Glu
                    325                 330                 335

Arg Gly Ile Val Leu Thr Pro Asp Ile Leu Thr Asn Ala Gly Gly Val
                340                 345                 350

Thr Val Ser Tyr Phe Glu Trp Val Gln Asn Leu Tyr Gly Tyr Tyr Trp
            355                 360                 365

Ser Glu Glu Glu Val Glu Gln Lys Glu Ile Ala Met Val Lys Ala
    370                 375                 380

Phe Glu Ser Ile Trp Lys Ile Lys Glu Glu Tyr Asn Val Thr Met Arg
385                 390                 395                 400

Glu Ala Ala Tyr Met His Ser Ile Lys Lys Val Ala Glu Ala Met Lys
                    405                 410                 415

Leu Arg Gly Trp Tyr
                420

<210> SEQ ID NO 2
<211> LENGTH: 448
<212> TYPE: PRT
<213> ORGANISM: Clostridium perfringens

<400> SEQUENCE: 2

Met Glu Val Lys Lys Tyr Val Asp Asn Leu Met Glu Asp Leu Lys Lys
1               5                   10                  15

Asn Asn Pro Gly Glu Ser Glu Phe Leu Ala Ala Glu Glu Val Leu
            20                  25                  30

Tyr Ser Leu Val Pro Val Leu Glu Lys Asn Pro Lys Tyr Met Glu Glu
        35                  40                  45

Gly Ile Leu Glu Arg Ile Val Glu Pro Glu Arg Val Ile Met Phe Arg
    50                  55                  60

Val Pro Trp Val Asp Asp Ala Gly Asn Val Arg Val Asn Arg Gly Tyr
65                  70                  75                  80

Arg Val Gln Phe Asn Ser Ala Ile Gly Pro Tyr Lys Gly Gly Leu Arg
                85                  90                  95

Phe His Pro Ser Val Asn Leu Ser Ile Lys Phe Leu Gly Phe Glu
            100                 105                 110

Gln Ile Phe Lys Asn Ser Leu Thr Thr Leu Pro Ile Gly Gly Gly Lys
        115                 120                 125

Gly Gly Ser Asn Phe Asp Pro Lys Gly Lys Ser Asp Arg Glu Ile Met
    130                 135                 140

Arg Phe Cys Gln Ser Phe Met Ser Glu Leu Tyr Arg His Ile Gly Pro
145                 150                 155                 160
```

```
Asn Thr Asp Val Pro Ala Gly Asp Ile Gly Val Gly Gly Arg Glu Ile
            165                 170                 175

Gly Tyr Met Phe Gly Gln Tyr Lys Lys Leu Lys Asn Ser Val Asp Ala
            180                 185                 190

Gly Val Leu Thr Gly Lys Gly Leu Thr Tyr Gly Gly Ser Leu Ala Arg
            195                 200                 205

Lys Glu Ala Thr Gly Tyr Gly Leu Val Tyr Phe Val Asp Glu Met Leu
            210                 215                 220

Arg Asp Asn Gly Gln Thr Ile Glu Gly Lys Thr Val Ile Ser Gly
225                 230                 235                 240

Ser Gly Asn Val Ala Ile Tyr Ala Thr Glu Lys Val Gln Glu Leu Gly
            245                 250                 255

Gly Lys Val Val Ala Leu Ser Asp Ser Ser Gly Tyr Val Tyr Asp Glu
            260                 265                 270

Asn Gly Ile Asp Leu Glu Val Lys Glu Ile Lys Glu Val Lys Arg
            275                 280                 285

Gly Arg Ile Ser Glu Tyr Val Asn Tyr Val Lys Thr Ala Lys Phe Thr
            290                 295                 300

Glu Gly Phe Arg Gly Ile Trp Asn Val Lys Cys Asp Ile Ala Leu Pro
305                 310                 315                 320

Cys Ala Thr Gln Asn Glu Ile Asp Lys Ser Ser Ala Lys Thr Leu Ile
            325                 330                 335

Asp Asn Gly Val Ile Ala Val Gly Gly Ala Asn Met Pro Ser Thr
            340                 345                 350

Leu Glu Ala Gln Lys Leu Phe Val Asp Asn Lys Ile Leu Phe Ala Pro
            355                 360                 365

Ala Lys Ala Ala Asn Ala Gly Gly Val Ala Thr Ser Ala Leu Glu Met
            370                 375                 380

Ser Gln Asn Ser Leu Arg Met Ser Trp Thr Phe Glu Glu Val Asp Ala
385                 390                 395                 400

Lys Leu Lys Asp Ile Met Lys Asn Ile Tyr Tyr Asn Ser Arg Asn Ala
            405                 410                 415

Ala Ser Glu Tyr Gly His Asp Gly Asn Leu Ile Val Gly Ala Asn Ile
            420                 425                 430

Ala Gly Phe Lys Lys Val Ala Asp Ala Met Leu Asp His Gly Ile Ile
            435                 440                 445

<210> SEQ ID NO 3
<211> LENGTH: 421
<212> TYPE: PRT
<213> ORGANISM: Clostridium botulinum

<400> SEQUENCE: 3

Met Ala Lys Glu Asn Leu Asn Pro Phe Glu Asn Ala Gln Lys Gln Val
1               5                   10                  15

Lys Thr Ala Cys Asp Lys Leu Gly Met Glu Pro Ala Val Tyr Glu Leu
            20                  25                  30

Leu Lys Glu Pro Gln Arg Val Ile Glu Val Ser Ile Pro Val Lys Met
            35                  40                  45

Asp Asp Gly Ser Val Lys Val Phe Lys Gly Tyr Arg Ser Gln His Asn
            50                  55                  60

Asp Ala Val Gly Pro Thr Lys Gly Gly Val Arg Phe His Pro Asn Val
65                  70                  75                  80

Ser Leu Asp Glu Val Lys Ala Leu Ser Ile Trp Met Thr Phe Lys Cys
            85                  90                  95
```

```
Ser Val Thr Gly Ile Pro Tyr Gly Gly Gly Lys Gly Gly Ile Ile Val
            100             105             110

Asp Pro Lys Thr Leu Ser Lys Gly Glu Leu Glu Arg Leu Ser Arg Gly
            115             120             125

Tyr Ile Asp Gly Ile His Lys Leu Ile Gly Glu Lys Val Asp Val Pro
            130             135             140

Ala Pro Asp Val Asn Thr Asn Gly Gln Ile Met Ala Trp Met Val Asp
145             150             155             160

Glu Tyr Asn Lys Leu Val Gly Arg Ser Ala Ile Gly Val Ile Thr Gly
            165             170             175

Lys Pro Val Glu Phe Gly Gly Ser Leu Gly Arg Asn Ala Ala Thr Gly
            180             185             190

Phe Gly Val Ala Val Thr Ala Arg Glu Ala Ala Ala Lys Leu Gly Ile
            195             200             205

Asp Met Lys Lys Ala Lys Leu Ala Ile Gln Gly Ile Gly Asn Val Gly
            210             215             220

Ser His Thr Val Leu Asn Cys Glu Lys Leu Gly Gly Thr Val Val Ala
225             230             235             240

Leu Ala Glu Trp Cys Lys Glu Glu Gly Thr Tyr Ala Ile Tyr Asn Glu
            245             250             255

Asn Gly Leu Asp Gly Lys Ala Met Ile Glu Tyr Val Lys Glu Asn Gly
            260             265             270

Asn Leu Leu Gly Tyr Pro Gly Ala Lys Lys Ile Ser Leu Asp Glu Phe
            275             280             285

Trp Ala Leu Asn Val Asp Ile Leu Ile Pro Ala Ala Leu Glu Asn Ala
            290             295             300

Ile Thr His Glu Asn Ala Ser Ser Ile Asn Ala Lys Leu Val Cys Glu
305             310             315             320

Ala Ala Asn Gly Pro Ile Thr Pro Asp Ala Asp Ala Ile Leu Lys Glu
            325             330             335

Lys Gly Ile Thr Val Thr Pro Asp Ile Leu Thr Asn Ala Gly Gly Val
            340             345             350

Thr Val Ser Tyr Phe Glu Trp Val Gln Asn Leu Tyr Gly Tyr Tyr Trp
            355             360             365

Thr Glu Ala Glu Val Glu Ala Lys Glu Glu Ala Met Val Lys Ala
            370             375             380

Phe Glu Ser Ile Trp Ala Ile Lys Glu Glu Tyr Ser Val Thr Met Arg
385             390             395             400

Glu Ala Ala Tyr Met His Ser Ile Lys Lys Val Ala Gly Ala Met Lys
            405             410             415

Leu Arg Gly Trp Tyr
            420
```